(12) United States Patent
Rodriguez

(10) Patent No.: US 7,256,184 B2
(45) Date of Patent: Aug. 14, 2007

(54) TREATMENT OF AGING DISORDERS IN HUMANS

(76) Inventor: Victorio C. Rodriguez, 7791 Hoertz Rd., Parma, OH (US) 44134

( * ) Notice: Subject to any disclaimer, the term of this patent is extended or adjusted under 35 U.S.C. 154(b) by 399 days.

(21) Appl. No.: 10/858,091

(22) Filed: Jun. 1, 2004

(65) Prior Publication Data
US 2004/0253223 A1 Dec. 16, 2004

Related U.S. Application Data

(63) Continuation-in-part of application No. 10/077,719, filed on Feb. 15, 2002, now Pat. No. 6,821,997, which is a continuation-in-part of application No. 09/688,290, filed on Oct. 16, 2000, now abandoned.

(51) Int. Cl.
| | |
|---|---|
| A61K 31/593 | (2006.01) |
| A61P 25/00 | (2006.01) |
| A61P 25/18 | (2006.01) |
| A61P 25/24 | (2006.01) |
| A61P 25/28 | (2006.01) |

(52) U.S. Cl. ................ 514/167; 514/878; 514/879; 514/903

(58) Field of Classification Search ............ 514/167, 514/168, 878, 879
See application file for complete search history.

(56) References Cited

U.S. PATENT DOCUMENTS

| | | | | |
|---|---|---|---|---|
| 5,929,028 | A * | 7/1999 | Skrabanja et al. ............ 514/2 |
| 5,939,407 | A * | 8/1999 | Landfield .................. 514/167 |
| 6,051,566 | A * | 4/2000 | Bianco ..................... 514/165 |
| 6,552,053 | B2 | 4/2003 | Sun et al. |
| 6,933,278 | B1 * | 8/2005 | Vickers et al. .............. 514/12 |
| 6,979,468 | B1 * | 12/2005 | Pollard ..................... 424/643 |
| 7,045,513 | B1 * | 5/2006 | Parasrampuria et al. .... 514/170 |

OTHER PUBLICATIONS

Medline abstract, accession No. 2004372399 (2004).*
Medline abstract, accession No. 2002203050 (May 2002).*
Medline abstract, accession No. 97434650 (1997).*
Medline abstract, accession No. 92304336 (1992).*
Medline abstract, accession No. 2002058763 (Feb. 2002).*
Medline abstract, accession No. 2001264687 (2001).*
Medline abstract, accession No. 2001391287 (2001).*
"Estrogen Study on Menopausal Women Is Stopped" by Brown, *Washington Post*, Wednesday, Mar. 3, 2004.
Abstract—"Progestins initiative adverse events of menopausal estrogen therapy" by Thomas, et al., *Climacteric* (2003), 6(4), 293-301.
Abstract—"Effects of rofecoxib or naproxen vs. placebo on Alzheimer disease progression" by Aisen, et al., *JAMA, The Journal of the Amercian Medical Association* (2003), 289(21), 2819-2826.
Abstract—"Current status of metals as therapeutic targets in Alzheimer's disease" by Finefrock, et al., *Journal of the American Geriatrics Society*, (Aug. 2003) 51 (8) 1143-8.
Abstract—"Cysteamine-induced depletion of somatostatin produces differential cognitive deficits in rats" by DeNoble, et al., *Brain Research* (1989), 482(1), 42-8.
Abstract—"Defective phorbol ester-stimulated secretion of .beta.-amyloid precursor protein from Alzheimer's disease fibroblasts" by Bergamaschi, et al., *Neuroscient Letters*, (1995), 201(1), 1-4.
Abstract—"Age-dependent enzymatic changes in human cerebral cortex" by Reichlmeier, K., *Aktuelle Gerontol*, Aug. 1978, 8(8):441-8.
Abstract—"Neurochemical findings in the aging brain" by Meier-Ruge, et al., *Adv. Biochem Psychopharmacol*, 1980; 23:323-38.
Abstract—"Carbonic anydrase III. Oxidative modification in vivo and loss of phosphatase activity during Aging" by Cabiscol, et al., *J. Biol. Chem*. Jun. 16, 1995;270(24):14742-7.
Abstract—"Addition of carbonic anhydrase augments extracellular pH buffering in rat cerebral cortex" by Huang, et al., *J. Neurophysiol*, Oct. 1995;74(4):1806-9.
Abstract—"A comparative CD study of carbonic anhydrase isoenzymes with different number of tryptophans: impact on calculation of secondary structure content" by Boren, et al., *Protein Sci*., Dec. 1996;5(12):2479-84.
Abstract—"Nonsteroidal anti-inflammatory drugs activate carbonic anhydrase by a direct mechanism of action" by Puscas, et al., *J. Pharmacol. Exp Ther*, Jun. 1996;277(3):1464-6.
Abstract—"Efficacy of exogenous oral zinc in treatment of patients with carbonic anhydrase VI deficiency" by Henkin, et al., *Am J Med Sci* Dec. 1999;318(6):392-405.
Abstract—"Intracellular zinc depletion induces caspase activation and p21 Waf1/Dip1 cleavage in human epithelial cell lines" Chai, et al., *J Ifect Dis* Sep. 2000;182 Suppl 1:S85-92.

* cited by examiner

*Primary Examiner*—John Pak

(57) ABSTRACT

A method for the treatment and prophylaxis of conditions of aging in humans, such conditions of aging associated with a decreased presence of one or more cell-specific carbonic anhydrase enzymes. Such conditions include chronic neurodegenerative conditions including dementia such as Alzheimer's disease. The method comprises administering to the patient a pharmaceutically effective, non-toxic amount of a compound that increases the presence of one or more cell-specific carbonic anhydrase enzymes whose levels are reduced in the patient. Such compound may be the cell-specific carbonic anhydrase enzyme, a compound that when absorbed by the body reacts or dissociates to form the cell-specific carbonic anhydrase enzyme, or a compound that promotes the natural generation of the cell-specific carbonic anhydrase enzyme within the body.

15 Claims, 1 Drawing Sheet

Fig. 1

PATHOPHYSIOLOGY OF ALZHEIMER'S DISEASE AND OTHER
NEURODEGENERATIVE DISORDERS

A. Primary deficiency of cell-specific carbonic anhydrase enzyme due to defective gene-link carbonic anhydrase enzymes.
B. Secondary deficiency of cell-specific carbonic anhydrase enzyme due to:
   1. Neurotoxic materials, such as aluminum, iron, and lead
   2. Infections that alter the blood-brain barrier
   3. Amyloid deposits that alter the blood-brain barrier
   4. Other conditions or diseases that alter the blood-brain barrier that displace the zinc from cell-specific carbonic anhydrase enzymes

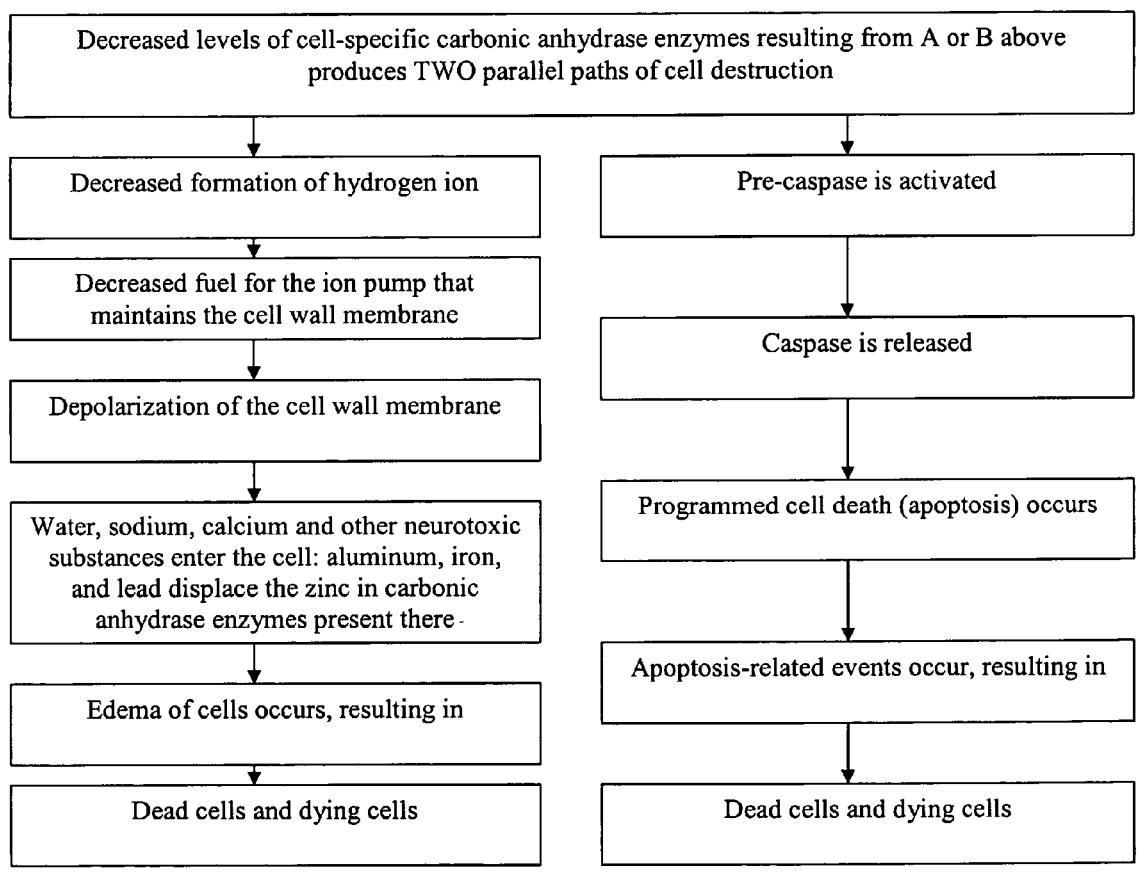

- DEAD AND DYING CELLS INCLUDE NEURONS (BRAIN CELLS) -
(Neuro-fibrillary tangles and tau proteins)

TREATMENT OF AGING DISORDERS IN HUMANS

CROSS-REFERENCE TO RELATED APPLICATIONS

This application is a continuation-in-part application of the U.S. patent application Ser. No. 10/077,719, filed on Feb. 15, 2002, now U.S. Pat. No. 6,821,997, which is a continuation-in part of U.S. patent application Ser. No. 09/688,290, filed on Oct. 16, 2000, now abandoned.

FIELD OF THE INVENTION

This invention deals with therapeutic and prophylactic treatment of age-related problems or disorders, including age-related neurological disorders, in human patients.

BACKGROUND OF THE INVENTION

Normal aging in humans is recognized as producing some or all of the following typical physiological results:
1. Brain weight is reduced by 15%
2. Blood flow to the brain is reduced by 20%
3. Body water content is reduced by 18%
4. Body weight is reduced by 12%
5. Nerve conduction velocity is reduced by 10%
6. Number of nerve fibers in nerves are reduced by 37%
7. Decreased amounts of enzymes and coenzymes
8. Decreased amounts of neurotransmitters
9. Depletion of oxidative, phosphorelative enzymes
10. Apoptosis—chronic neuronal atrophy In describing their work in an article entitled "Studies on Age-Dependent Ozonide Changes in Human Cerebral Cortex," (by Reichlmeier K., Ermini M., and Schlecht H. P.—*Aktuelle Gerontol* 1978 August 8(8):44-8), the authors report that they investigated the activity of various enzymes of human brains obtained at autopsy and covering an age range of 19 to 91 years. Protein kinase, which mediates the information carried by the second messenger, cyclic AMP (3', 5'-cyclic adenosine monophosphate), does not show age-related changes of basal activity. Cyclic AMP-dependent activation of protein kinase remains nearly constant up to 60 years of life, but it undergoes a distinct and progressive decline between 60 and 90 years. In the corpus striatum, no age related changes of cyclic AMP-dependent protein kinase activity were observed. The activity of carbonic anhydrase exhibits, in both human cortex and corpus striatum, an age-dependent decrease that also begins after the sixth decade of life.

SUMMARY OF THE INVENTION

The present invention provides methods for the treatment and prophylaxis of conditions of aging in human patients. Such conditions of aging include, but are not limited to, chronic neurodegenerative conditions, including dementia such as Alzheimer's disease. The method comprises: assaying for a reduced or decreased level of one or more carbonic anhydrase isozymes in a tissue of the patient and then administering one or more compounds that increase the level of one or more carbonic anhydrase isozymes that are present at reduced levels in a tissue of the patient. In certain embodiments, the tissue is blood, cerebro-spinal fluid, or a biopsied tissue of the patient. A finding that the tissue level of one or more carbonic anhydrase isozymes is decreased is based upon comparison with a control value derived from healthy young human subjects. In certain embodiments, the method comprises administering one or more carbonic anhydrase enzymes, either synthetically-produced or naturally-produced, to the patient. In another embodiment, the method comprises administering one or more compounds that, when absorbed by a tissue of the patient, reacts or dissociates to form one or more carbonic anhydrase isozymes that are present at reduced levels in the patient. In another embodiment the method comprises administering one or more compounds that induce or promote the generation of one or more carbonic anhydrase enzymes that are present at reduced levels in the patient. In certain embodiments the compounds are administered over an extended period of time, ranging from 6 months to 5 years.

BRIEF DESCRIPTION OF THE DRAWINGS

FIG. 1 illustrates the pathophysiology of neurodegenerative disorders.

DETAILED DESCRIPTION OF THE INVENTION

The present invention will now be described by reference to more detailed embodiments, with occasional reference to the accompanying drawing. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

The following represents an essential chemical reaction that takes place in human tissue

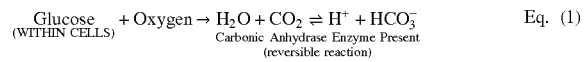

$$\underset{\text{(WITHIN CELLS)}}{\text{Glucose}} + \text{Oxygen} \rightarrow \underset{\substack{\text{Carbonic Anhydrase Enzyme Present} \\ \text{(reversible reaction)}}}{H_2O + CO_2 \rightleftharpoons H^+ + HCO_3^-} \qquad \text{Eq. (1)}$$

Glucose is irreversibly oxidized within the cells to produce water and carbon dioxide. In the presence of a catalyst, especially a carbonic anhydrase enzyme (of which several forms exist, of which the form present depends upon the type of tissue cells present), the water and carbon dioxide reversibly produce a hydrogen ion and a bicarbonate ion.

Carbonic anhydrase is a zinc-containing enzyme that catalyzes the reversible $CO_2$ hydration reaction illustrated in Eq. 1. The mitochondria of cells of different tissues and organs produces different specific carbonic anhydrase enzymes that maintain the equilibrium of the above equation in all spaces—cellular, interstitial, and vascular—as illustrated in FIG. 1. At least seven carbonic anhydrase variants, called "s" have been identified. The literature may refer to these as "carbonic anhydrases I through VII" or "CAS I-VII". We here refer to this selectivity as "cell-specific" and the particular carbonic anhydrase present as being a "cell-specific carbonic anhydrase enzyme."

Hydrogen ion produced by carbonic anhydrase enzymes is acted upon by cytochrome system, which is then utilized as the energy source of the ion pump that maintains the integrity of the cell membrane comprising and enclosing each cell. It is also thought to be a source of the brain's electric current. The process is schematically illustrated in FIG. 1, presented here with no further discussion.

Disruption of the process that included Eq. 1 causes depolarization of the cell wall membrane, hence sodium (Na), water ($H_2O$), and other chemicals can enter the cell in uncontrolled amounts and potassium (K) can exit uncontrollably, leading to the death and destruction of the involved cells; cellular edema follows. As this edema progresses, the cell dies. Along with the progressive and gradual death of cells, gliosis follows—hence aging in the brain occurs.

Carbonic anhydrase enzyme has been used to augment the extracellular pH buffering in the cerebral cortex of rats (*Journal of Neurophysiology* 1995 Oct. 74(4):1806-9). It is known that the blood-brain barrier in animals is incomplete compared to that of humans where the blood-brain barrier is complete and a formidable barrier to chemical transport. Substances that prove efficacious in affecting the brain chemistry of animals are not necessarily efficacious in the brains of human beings because they cannot pass through the more complete blood-brain barrier in humans. Although some researchers equivocate on this concept, most of the medical community accepts the idea that carbonic anhydrase enzymes traverse the blood-brain barrier in humans as fact, especially regarding the carbonic anhydrase enzyme referred to as CA-II.

As far as can be determined from the literature, cell-specific carbonic anhydrase enzymes have never been used to restore to a higher level the carbonic anhydrase enzymes that are lacking due to decreased levels due to normal aging. At least some of the carbonic anhydrases have been extracted from animal tissue, isolated, and studied for molecular structure. This shows that the enzymes can be isolated and made available for administration to a patient for therapeutic or prophylactic treatment.

In U.S. Pat. No. 5,972,684, Bandman et al. tell us:

"Eight enzymatic and evolutionary related forms of carbonic anhydrase are currently known to exist in humans: three cytosolic s (CAI, CAII, and CAIII), two membrane-bound forms (CAIV and CAVII), a mitochondrial form (CAV), a secreted salivary form (CAVI) and a yet uncharacterized. Isoforms show a characteristic motif. (See, e.g., http//expasy.hcuge.ch). Though the s CAI, CAII and bovine CAIII have similar secondary structure and polypeptide-chain fold, CAI has 6 tryptophans, CAII has 7 and CAIII has 8 (Boren, K. et al. (1996) Protein Sci. 5(12):2479-2484). CAII is the predominant CA isoenzyme in the brain of mammals."

"Inhibition and activation of CA provide information about CA structure and activity. Vasodilating prostaglandins E1, E2 and I2 inhibit CA in vitro and in vivo and may inhibit the involvement of CA in gastric acid secretion. Nonsteroidal anti-inflammatory drugs which reduce the activity of cyclooxygenase and prostaglandin production have also been observed to activate CAI and CAII in a dose-dependent noncompetitive manner. The pre-prostaglandin cyclooxygenase appears to maintain an inverse relationship with CA, probably mediated by the pH variations associated with carbonic anhydrase activity (Puscas, I (1996) J. Pharmacol. Exp. Ther. 277(3):1464-1466). Both prostaglandins E2 and I2 inhibit gastric acid output. Prostaglandin E2 inhibits egress of norepinephrine from sympathetic nerve terminals.

The Bandman et al. patent teaches another carbonic anhydrase, CA-VIII, the subject of their patent. The present patent does not deal with nor address CA-VIII.

Patients having a carbonic anhydrase VI (CA-VI) deficiency have been treated with orally-administered zinc in an effort to stimulate the synthesis/secretion of CA-VI and the successful results were reported in the American Journal of Medical Science (Efficacy of exogenous oral zinc in treatment of patients with carbonic anhydrase VI deficiency, by Henkin, R. I., Martin, B. M., and Agarwal, R. P.—*Am J Med Sci* 1999 Dec. 3; 18(6):392-405). Thus, it is shown that the synthesis/secretion of carbonic anhydrase can, indeed, be stimulated by compounds administered orally.

Referring to FIG. 1, we observe two parallel paths of cell destruction that can be directly linked to deficiencies of cell-specific carbonic anhydrase enzymes, whether the decreased level of CA is a primary deficiency or a secondary deficiency, as described therein. One path relates to the breakdown of the chemical reaction shown in Eq. 1 and the other relates to the release of caspase, leading to apoptosis. The result of both paths is dead cells and dying cells, which include brain cells and other neural cells. Here we show that at least one cause of the destruction of brain cells and other neurons is traceable to decreased levels of cell specific carbonic anhydrase enzymes.

Heretofore, researchers had identified only one of these parallel paths, the one involving caspase. Specifically, it has been reported in the Journal of Infectious Diseases, 2000 September; 182 Suppl 1:S85-92, by F. Chai, et al. that the mechanism by which zinc deficiency (equivalent to deficiency in zinc-carrying carbonic anhydrase enzyme) induces epithelial cell death involves the activation of caspase-3 as indicated in the right half of FIG. 1. The suggestion is made from this research that zinc (i.e., CA) may suppress a step just before the activation of the caspase and a zinc (i.e., CA) deficiency results in a failure to suppress that step.

The path illustrated on the left half of FIG. 1 is newly presented in the instant invention. The decreased levels of CA (i.e., zinc-carrying enzyme) upset the rate of the reversible portion of the reaction indicated in Eq. 1, above, decreasing the formation of hydrogen ion that is the fuel for the ion pump that maintains the cell wall membrane, leading to depolarization and allowing neurotoxic substances to enter the cell, causing edema and cell death.

Whereas in aging, there has been observed a progressive decrease in levels of enzymes of which carbonic anhydrase is one, I believe that replenishing the carbonic anhydrase enzymes that catalyze the reversible reaction of Equation 1 will at least slow the progressive and gradual death of cells, including cells in the brain, which brain cell reduction is a major contributor to various age-related brain disorders involving dementia such as Alzheimer's disease, and neurodegenerative diseases.

Cell-specific carbonic anhydrase enzymes have never been used to restore to a higher level the carbonic anhydrase enzymes that are lacking due to decreased levels due to normal aging, whether the replenishing enzymes are naturally-produced and harvested or synthetically-produced, nor has anyone used for this purpose any carbonic anhydrase stimulators to stimulate a patient's production of carbonic andydrase enzymes.

I have come to the realization that administering supplemental cell-specific carbonic anhydrase enzymes or administering cell-specific carbonic anhydrase enzyme stimulators, the effects of aging, especially in the central nervous system, by raising the level of cell-specific carbonic anhydrase enzymes present. In using the term "stimulators" I mean to include materials for stimulating the production of cell-specific carbonic anhydrase enzymes. Another method for raising the level of the required enzymes is to directly administer the enzymes themselves. These techniques are available in the medical literature for extracting naturally-produced enzymes.

This treatment can be administered to patients exhibiting signs of Alzheimer's disease or showing other forms of dementia or neurodegenerative diseases. It is also feasible to administer this treatment as a prophylactic or preventative to an aging patient to prevent or at least delay the onset of such dementia, from whatever cause. The present treatment can also be used to prevent or inhibit the progress of other age-related disorders in patients who have a family history or who are exhibiting symptoms of such disorders. Examples of such age-related disorders include, but are not limited to, age-related disorders of the bone, including osteoporosis; age-related disorders of the musculoskeletal system, including arthritis and myopathies; and age-related disorders of the integumentary system, including wrinkling of the skin.

Thus, I disclose here a method for the treatment and prophylaxis of conditions of aging associated with decreased presence of cell-specific carbonic anhydrase enzymes in the brain, such as conditions associated with chronic neurodegenerative conditions including dementia such as Alzheimer's disease, which method comprises the administration over an extended period of time in the range of six months to five years, of a pharmaceutically effective, non-toxic amount of a compound that increases the presence of a cell-specific carbonic anhydrase enzyme in the brain. The carbonic anhydrase enzyme found most abundantly in the brain is referred to CA-II; the method may be applied to other carbonic anhydrase enzymes as well as to CA-II.

The compound used could be the cell-specific enzyme that is believed to be evidencing a decreased presence as measured in blood tests or in cell cultures of brain cells from biopsied tissues or from cerebro-spinal fluid. Alternatively, the compound used could be synthetically produced cell-specific carbonic anhydrase enzyme. As another alternative, the compound used could be naturally-produced cell-specific carbonic anhydrase enzyme. Yet another alternative allows that the compound used is a compound that, when administered to a human patient, promotes the natural production of the cell-specific enzyme that is evidencing a decreased presence as measured in blood tests or in cell cultures of brain cells from biopsied tissues or from cerebro-spinal fluid. The compound itself need not be one that passes the blood-brain barrier; the cell-specific enzyme need not be produced within the brain for it is known to pass the blood-brain barrier so the promoting of the natural production of cell-specific enzyme can take place elsewhere in the body.

Examples of compounds that are known to promote the natural production of the required cell-specific enzyme include, but are not limited to, zinc; growth hormone; a sex hormone; an androgen, including dihydroepiandrosterone (DHEA); a non-steroidal anti-inflammatory drug, including indomethacin; 1,25-dihydroxyvitamin D3; phorbol myristate acetate; cysteamine; selective serotonin reuptake inhibitors; histamine and a derivative of histamine, provided that the histamine derivative is not a sulfonylamido derivative of histamine. For instance, the sex hormones androgen and estrogen are known to increase the production of carbonic anhydrase III. Vitamin D3 increases the production of carbonic anhydrase II. Zinc increases the production of carbonic anhydrase VI. Growth hormone increases the production of carbonic anhydrase III. The non-steroidal anti-inflammatory drug including indomethacin increases the production of carbonic anhydrase I and II. Histamine and cysteamine increase production of carbonic anhydrase isozymes I, II, and IV. The selective serotonin reuptake inhibitors sertraline, fluoxetine, and citalopram increase production of carbonic anhydrase isozymes I and II. Phorbol myristate acetate increases production of carbonic anhydrase II Administering the compound may be done by injection or ingestion. The injection method used may be intramuscular or intravenous, dissolved in a sterile saline solution, glucose solution, or other commonly-administered parenteral solution. The best method of administering the compound will be learned with modest experimentation. The individual patient's response to the compound will be learned through testing for the cell-specific enzyme in blood samples taken before and after administering the medication and by enzyme levels measured from cell cultures of brain cells from biopsied tissues or found in cerebro-spinal fluid. The goal is to increase the tissue level of the cell-specific enzyme in the patient from its reduced level to a more normal level. Insofar as the enzyme level in the blood is a reflection of the enzyme level in the brain, the blood tests may be a sufficient indicator. In addition, and other means of measuring enzyme levels that are known to the practitioner may be employed.

Pharmaceutical compositions suitable for use in the invention include compositions wherein the active ingredients are contained in an effective amount to achieve the intended purpose. The determination of an effective dose is well within the capability of those skilled in the art.

A therapeutically effective dose refers to that amount of active ingredient that ameliorates the symptoms or condition, the condition being caused by or reflected in reduced concentration of carbonic anhydrase. Therapeutic efficacy and toxicity may be determined by standard procedures from blood testing, from biopsied tissues, and by other means known to the practitioner, for comparison with the normal values. The dosage is preferably within a range of circulating concentrations that are efficacious with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect, which is a near-normal level so the cell-specific enzyme. Factors which may be taken into account include the severity of the enzyme reduction extant in the subject, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formation.

Normal dosage amounts may vary from 0.1 to 100,000 micrograms, up to a total dose of about 1 gram, depending upon the route of administration. Guidance as to particular dosages and methods of delivery is provided in the literature and generally available to practitioners in the art. Those skilled in the art will employ different formulations to achieve the desired results.

I claim:

1. A method for the treatment of a condition of aging in a human patient comprising:
   (a) assaying for a decrease in the level of one or more carbonic anhydrase isozymes in a tissue of a human patient suspected of having a condition of aging selected from the group consisting of dementia, neurodegenerative disease, Alzheimer's disease and combinations thereof;
   (b) selecting the human patient whose assay shows a decrease in the level of one or more carbonic anhydrase isozymes; and
   (c) administering to the selected patient a pharmaceutically effective amount of 1,25-dihydroxyvitamin $D_3$ to increase the level of one or more carbonic anhydrase isozymes that are present at decreased levels in the patient;
   wherein the patient has reduced symptoms and signs of dementia, neurodegenerative disease, Alzheimer's disease or a combination thereof after being administered the pharmaceutically effective amount of 1,25-dihydroxyvitamin $D_3$.

2. The method of claim 1, wherein step (a) comprises determining the levels of carbonic anhydrase (CA)-I, carbonic anhydrase (CA)-II, carbonic anhydrase (CA)-III, carbonic anhydrase (CA)-IV, carbonic anhydrase (CA)-V, carbonic anhydrase (CA)-VI, carbonic anhydrase (CA)-VII, or any combination thereof in the blood of the patient.

3. The method of claim 1, wherein said 1,25-dihydroxyvitamin D3, when administered to the human patient, promotes the production in the patient of one or more carbonic anhydrase isoenzymes that is present at decreased levels in a tissue of the patient.

4. The method of claim 1, wherein said administering is by injection.

5. The method of claim 4, wherein said injection is intramuscular.

6. The method of claim 4, wherein said injection is intravenous.

7. The method of claim 1, wherein said administering is by ingestion.

8. The method of claim 1, wherein step (a) comprises determining the levels of carbonic anhydrase (CA) I, carbonic anhydrase (CA) II, carbonic anhydrase (CA) III, carbonic anhydrase (CA) IV, carbonic anhydrase (CA) V, carbonic anhydrase (CA) VI, carbonic anhydrase (CA) VII, or any combination thereof in the cerebrospinal fluid of the patient.

9. The method of claim 1, wherein step (a) comprises determining the levels of carbonic anhydrase (CA) I, carbonic anhydrase (CA) II, carbonic anhydrase (CA) III, carbonic anhydrase (CA) IV, carbonic anhydrase (CA) V, carbonic anhydrase (CA) VI, carbonic anhydrase (CA) VII, or any combination thereof in a biopsied tissue of the patient.

10. The method of claim 1, wherein the patient is exhibiting symptoms of a chronic neurodegenerative condition.

11. The method of claim 1, wherein the patient is exhibiting symptoms of a dementia.

12. The method of claim 1, wherein the patient has a family history of a dementia.

13. The method of claim 1, wherein the condition of aging is dementia.

14. The method of claim 1, wherein the condition of aging is a neurodegenerative disease.

15. The method of claim 1, wherein the condition of aging is Alzheimer's disease.

* * * * *